United States Patent [19]

Takago et al.

[11] 4,294,975
[45] Oct. 13, 1981

[54] HYDROALKENYLOXYSILANES

[75] Inventors: Toshio Takago; Masatoshi Arai; Koji Futatsumori, all of Annaka, Japan

[73] Assignee: Shin-Etsu Chemical Co. Ltd., Tokyo, Japan

[21] Appl. No.: 151,696

[22] Filed: May 20, 1980

[30] Foreign Application Priority Data

May 31, 1979 [JP] Japan .................................. 54/67706

[51] Int. Cl.$^3$ ............................. C07F 7/04; C07F 7/18
[52] U.S. Cl. ..................................... 556/482; 556/483
[58] Field of Search ................................ 556/482, 483

[56] References Cited

U.S. PATENT DOCUMENTS 3,299,173  1/1967  Roselli ............................. 556/483 X
3,472,888  10/1969  Bazouin et al. ................. 556/482 X

FOREIGN PATENT DOCUMENTS 1439013  4/1966  France ................................. 556/482
1495716  9/1967  France ................................. 556/482
1096033  12/1967  United Kingdom ................. 556/482

Primary Examiner—Paul F. Shaver

Attorney, Agent, or Firm—Toren, McGeady & Stanger

[57] ABSTRACT

The invention provides a novel class of organosilicon compounds which are hydrogenalkenyloxysilanes represented by the general formula

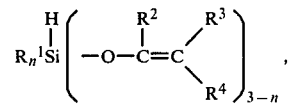

in which $R^1$ is a monovalent hydrocarbon group having from 1 to 8 carbon atoms, $R^2$, $R^3$ and $R^4$ are each a hydrogen atom or a monovalent hydrocarbon group having from 1 to 8 carbon atoms and n is a number of zero, 1 or 2. The silane compounds are readily obtained by the dehydrochlorination reaction between a corresponding hydrogen-containing chlorosilane compound and an $\alpha$, $\beta$-unsaturated aldehyde compound or a ketone compound in the presence of an acid acceptor. The compounds are useful as a modifying agent in the silicone technology and also serve as a curing agent.

5 Claims, No Drawings

HYDROALKENYLOXYSILANES

BACKGROUND OF THE INVENTION

The present invention relates to a novel class of organosilicon compounds hitherto unknown and useful for the modification of various silicone materials as well as for accelerating curing of crosslinkable silicone materials. The invention also relates to a method for the preparation of the above novel organosilicon compounds.

SUMMARY OF THE INVENTION

The novel organosilicon compound of the invention is a hydrogenalkenyloxysilane represented by the general formula

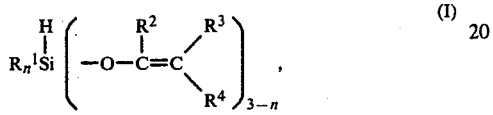

in which $R^1$ is a monovalent hydrocarbon group having from 1 to 8 carbon atoms, $R^2$, $R^3$ and $R^4$ are each independently a hydrogen atom or a monovalent hydrocarbon group having from 1 to 8 carbon atoms and n is a number of zero, 1 or 2.

The above defined hydroalkenyloxysilane is readily synthesized by the dehydrohalogenation reaction of a corresponding hydrogenhalogenosilane compound and an α,β-unsaturated aldehyde compound or a ketone compound in the presence of an acid acceptor.

DETAILED DESCRIPTION OF THE PREFERRED EMBODIMENTS

The inventive hydrogenalkenyloxysilane defined above is a novel compound hitherto unknown and not described in any literatures. The compound is represented by the above given general formula (I) in which $R^1$ is a monovalent hydrocarbon group having from 1 to 8 carbon atoms exemplified by alkyl groups such as methyl, ethyl, propyl, butyl and octyl group, alkenyl groups such as vinyl and allyl groups, aryl groups such as phenyl and tolyl groups and aralkyl groups such as benzyl and phenylethyl groups as well as those groups derived from the above named hydrocarbon groups by the substitution with halogen atoms or cyano groups and the like for part or all of the hydrogen atoms therein. Needless to say, the group $R^1$ is not essential when the number n is equal to 3.

The groups represented by $R^2$, $R^3$ and $R^4$ are each a hydrogen atom or a monovalent hydrocarbon group having from 1 to 8 carbon atoms similar to those groups given for $R^1$ above. These groups can be the same ones or may be different from each other in a molecule.

Among numbers of the hydrogenalkenyloxysilanes in conformity with the general formula (I) and the definitions of the symbols, following particular compounds are prepared most easily and with high yields:

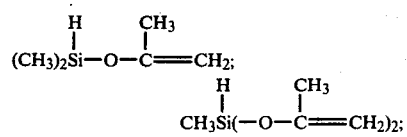

-continued

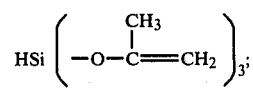

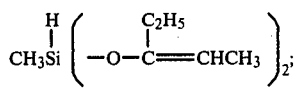

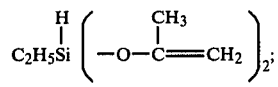

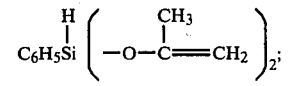

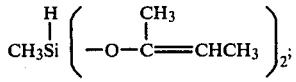

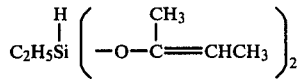

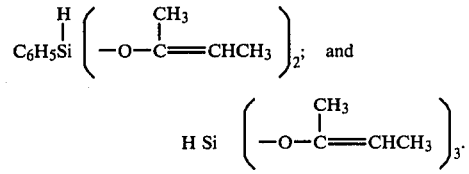

The inventive hydrogenalkenyloxysilane is readily synthesized by the dehydrohalogenation reaction, e.g. dehydrochlorination reaction between a corresponding hydrogen-containing chlorosilane compound and an α,β-unsaturated aldehyde compound or a ketone compound in the presence of an acid acceptor such as triethylamine at an elevated temperature with high yield.

In carrying out the above reaction, it is recommended to use the hydrogen-containing halogenosilane in an amount of not exceeding the equimolar amount to the aldehyde or ketone compound in order to obtain the desired product in a good yield relative to the starting silane compound. Further, the acid acceptor should be used in an amount in excess of equimolar. It is of course optional, if necessary, that the reaction mixture is diluted with a suitable organic solvent such as aromatic hydrocarbons, e.g. benzene, toluene and xylene, sliphatic hydrocarbons, e.g. hexane and pentane, and halogenated hydrocarbons, e.g. dichloroethane, trichloroethylene and perchloroethylene. It is sometimes recommended to use an excessive amount of the same aldehyde or ketone compound as that used as the reactant so as that the excess amount of the aldehyde or ketone may serve as a diluent of the reaction mixture. The reaction is usually carried out at a temperature in the range from 30° to 130° C. or, preferably, from 50° to 80° C. taking 6 to 8 hours. An excessively high temperature over 130° C. is undesirable due to the decrease in the yield of the desired product.

The hydrogenalkenyloxysilane of the invention is particularly useful as a modifying agent for various silicone materials or used as a curing agent. For example, the inventive silane compound reacts with an aliphatically unsaturated organic compound in the presence of a platinum catalyst by the addition reaction to give an alkenyloxysilyl adduct compound. The inventive silane compound is also useful for the modification of an organic polymer containing unsaturated groups with a silicone to give a modified polymer capable of being cured by the action of moisture in the presence of a trace amount of a catalyst.

Following are the examples to illustrate the inventive silane compounds and the method for the preparation thereof in further detail.

EXAMPLE 1

Into a reaction vessel were introduced 697 g (12 moles) of acetone and 608 g (6.0 moles) of triethylamine to form a reaction mixture into which 230 g (2.0 moles) of methyldichlorosilane were added dropwise over a period of 2 hours while keeping the temperature of the reaction mixture not to exceed 60° C. by cooling from outside.

After completion of addition of the silane compound, the reaction mixture was heated under reflux at about 60° C. for 2 hours to effect the reaction with precipitation of the hydrochloride of triethylamine. The triethylamine hydrochloride was removed by filtration and the filtrate was subjected to distillation under reduced pressure to give 269 g of a fraction boiling at 65° C. under a pressure of 85 mmHg.

The above obtained liquid product was identified by infrared absorption spectral analysis, mass spectrometric analysis, elementary analysis and NMR analysis (data given below) to be a hydrogenalkenyloxysilane expressed by the structural formula given below. The yield was about 85% of the theoretical value based on the amount of the starting silane compound used in the reaction.

$$CH_3Si\overset{H}{\underset{}{|}}\left(-O-\underset{CH_3}{\underset{|}{C}}=CH_2\right)_2$$

Infrared absorption spectral analysis:

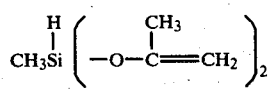   2180 cm$^{-1}$

Molecular weight by mass spectrometry: 158 (calculated molecular weight as $C_7H_{14}O_2Si$ 158)

Elementary analysis:

|    | Calculated as $C_7H_{14}O_2Si$, % | Found, % |
| --- | --- | --- |
| Si | 17.75 | 17.78 |
| C  | 53.12 | 53.10 |
| H  | 8.92  | 8.94 |

NMR analysis:

|   | δ value |
| --- | --- |
| Si—CH$_3$ | 0.28 |
| Si—H | 4.75 |
| C=CH$_2$ | 4.08 |
| —CH$_3$ | 1.76 |

EXAMPLE 2

The experimental procedure was substantially the same as in Example 1 except that the methyldichlorosilane was replaced with 203 g (1.5 moles) of trichlorosilane to give 160 g of a liquid product boiling at 43° C. under a pressure of 6 mmHg.

This liquid product was identified by the results of analyses given below to be a hydrogenalkenyloxysilane expressed by the structural formula given below. The yield was about 80% of the theoretical value based on the amount of the starting silane compound used in the reaction.

$$HSi\left(-O-\underset{CH_3}{\underset{|}{C}}=CH_2\right)_3$$

Infrared absorption spectral analysis:

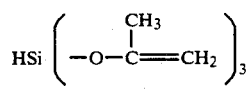   2220 cm$^{-1}$

Molecular weight by mass spectrometry: 200 (calculated molecular weight as $C_9H_{16}O_3Si$ 200)

Elementary analysis:

|    | Calculated as $C_9H_{16}O_3Si$, % | Found, % |
| --- | --- | --- |
| Si | 14.02 | 14.06 |
| C  | 53.96 | 53.93 |
| H  | 8.05  | 8.04 |

NMR analysis:

|   | δ value |
| --- | --- |
| —CH$_3$ | 1.62 |
|   | 4.01 |
|  |   |
|  | 4.34 |

EXAMPLE 3

Into a reaction vessel were introduced 275 g (4.73 moles) of acetone and 240 g (2.37 moles) of triethylamine to form a reaction mixture into which 150 g (1.58 moles) of dimethylchlorosilane were added dropwise over a period of 1 hour. After completion of addition of the silane, the reaction mixture was heated for 6 hours at about 60° C. to effect the reaction with precipitation of the hydrochloride of triethylamine. The triethylamine hydrochloride was removed by filtration and the filtrate was subjected to distillation to give 80 g of a liquid product boiling at 74° C. under atmospheric pressure.

The results of analyses shown below undertaken with this product indicated that this compound was a hydrogen alkenyloxysilane expressed by the structural formula below. The yield was about 43% of the theoretical value based on the amount of the starting silane compound used in the reaction.

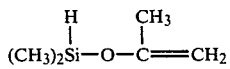

Infrared absorption spectral analysis:

 2130 cm$^{-1}$

Molecular weight by mass spectrometry: 116 (calculated molecular weight as $C_5H_{12}OSi$ 116)

Elementary analysis:

|    | Calculated as $C_5H_{12}OSi$, % | Found, % |
|----|---------------------------------|----------|
| Si | 24.17                           | 24.15    |
| C  | 51.66                           | 51.60    |
| H  | 10.41                           | 10.38    |

NMR analysis:

|                    | δ value |
|--------------------|---------|
| $\equiv$Si—CH$_3$  | 0.25    |
| $\equiv$Si—H       | 4.80    |
| $>$C=CH$_2$        | 3.86    |
| —CH$_3$            | 1.75    |

EXAMPLE 4

The experimental procedure was substantially the same as in Example 1 except that acetone was replaced with 697 g (8.1 moles) of diethylketone to give 257 g of a liquid product boiling at 86° C. under a pressure of 13 mmHg.

The results of analyses given below undertaken with this liquid product indicated that the product was a hydrogenalkenyloxysilane expressed by the structural formula given below. The yield was about 60% of the theoretical value based on the amount of the starting silane compound used in the reaction.

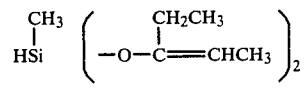

Infrared absorption spectral analysis:

 2170 cm$^{-1}$

Molecular weight by mass spectrometry: 214 (calculated molecular weight as $C_{11}H_{22}O_2Si$ 214)

Elementary analysis:

|    | Calculated as $C_{11}H_{22}O_2Si$, % | Found, % |
|----|--------------------------------------|----------|
| Si | 13.10                                | 13.13    |
| C  | 61.63                                | 61.68    |
| H  | 10.34                                | 10.30    |

What is claimed is:

1. A hydrogenalkenyloxysilane represented by the general formula

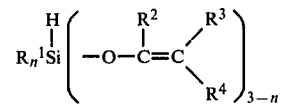

in which $R^1$ is a monovalent hydrocarbon group having from 1 to 8 carbon atoms, $R^2$, $R^3$ and $R^4$ are each independently a hydrogen atom or a monovalent hydrocarbon group having from 1 to 8 carbon atoms and n is a number of zero, 1 or 2.

2. The hydrogenalkenyloxysilane as claimed in claim 1 wherein $R^1$ is a methyl group, $R^2$ is a methyl group, $R^3$ and $R^4$ are each a hydrogen atom and n is 2.

3. The hydrogenalkenyloxysilane as claimed in claim 1 wherein $R^1$ is a methyl group, $R^2$ is a methyl group, $R^3$ and $R^4$ are each a hydrogen atom and n is 1.

4. The hydrogenalkenyloxysilane as claimed in claim 1 wherein $R^2$ is a methyl group, $R^3$ and $R^4$ are each a hydrogen atom and n is zero.

5. The hydrogenalkenyloxysilane as claimed in claim 1 wherein $R^1$ is a methyl group, $R^2$ is an ethyl group, $R^3$ is a hydrogen atom, $R^4$ is a methyl group and n is 1.

* * * * *